United States Patent
Davison

(10) Patent No.: US 9,375,297 B2
(45) Date of Patent: Jun. 28, 2016

(54) METHOD OF SURGICAL PLANNING

(71) Applicant: DePuy Synthes Products, Inc., Raynham, MA (US)

(72) Inventor: Andrew Charles Davison, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 512 days.

(21) Appl. No.: 13/788,742

(22) Filed: Mar. 7, 2013

(65) Prior Publication Data

US 2013/0310963 A1 Nov. 21, 2013

Related U.S. Application Data

(60) Provisional application No. 61/648,226, filed on May 17, 2012.

(51) Int. Cl.
  *A61C 13/00* (2006.01)
  *A61C 5/00* (2006.01)
(52) U.S. Cl.
  CPC .............. *A61C 13/0003* (2013.01); *A61C 5/007* (2013.01); *A61B 2034/102* (2016.02); *A61B 2090/363* (2016.02)
(58) Field of Classification Search
  None
  See application file for complete search history.

(56) References Cited

U.S. PATENT DOCUMENTS

| 6,671,539 | B2 | 12/2003 | Gateno et al. | |
|---|---|---|---|---|
| 7,574,025 | B2 | 8/2009 | Feldman | |
| 8,177,822 | B2 | 5/2012 | Medoff | |
| 2003/0065259 | A1* | 4/2003 | Gateno et al. | 600/425 |
| 2007/0197902 | A1* | 8/2007 | Schutyser | 600/416 |
| 2008/0123922 | A1 | 5/2008 | Gielen et al. | |
| 2010/0124731 | A1* | 5/2010 | Groscurth et al. | A61C 9/00 433/213 |
| 2011/0270583 | A1* | 11/2011 | Getto et al. | 703/1 |
| 2012/0022604 | A1 | 1/2012 | Polley et al. | |
| 2012/0062557 | A1* | 3/2012 | Dillon et al. | 345/419 |
| 2012/0141034 | A1 | 6/2012 | Iannotti et al. | |
| 2012/0150243 | A9 | 6/2012 | Crawford et al. | |

(Continued)

FOREIGN PATENT DOCUMENTS

EP    2428764    3/2012
WO    WO 2005/091978    10/2005

OTHER PUBLICATIONS

Sachdeva, R. C., "SureSmile Technology in a Patient-Centered Orthodontic Practice," Journal of Clinical Orthodontics, Apr. 2001, 35(4), 245-253.

(Continued)

*Primary Examiner* — Sean Shechtman
(74) *Attorney, Agent, or Firm* — Baker & Hostetler LLP

(57) ABSTRACT

A method of pre-operatively forming a surgical splint configured to receive a patient's dentition can include combining a 3-D facial computer model and a 3-D dental computer model. The method includes the step of obtaining a 3-D facial computer model of at least the patient's maxilla, mandible, and dentition from a CT scanner and the step of obtaining a 3-D dental computer model of the patient's dentition with an optical scanner. The 3-D dental computer model is then combined with the 3-D facial computer model to form a composite virtual model. The composite virtual model can be manipulated into a planned post-operative shape, and a surgical splint can be custom constructed to match the planned post-operative shape. The surgical splint can be configured to receive the patient's dentition.

20 Claims, 9 Drawing Sheets

(56) References Cited

U.S. PATENT DOCUMENTS

2012/0276509 A1 11/2012 Iannotti et al.
2012/0289965 A1 11/2012 Gelaude et al.

OTHER PUBLICATIONS

International Patent Application No. PCT/US2013/029564: International Search Report and Written Opinion dated Jun. 28, 2013, 10 pages.

* cited by examiner

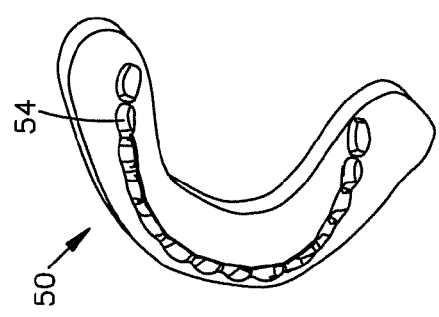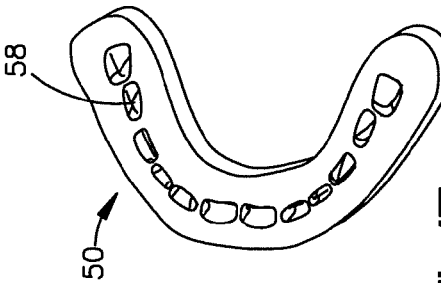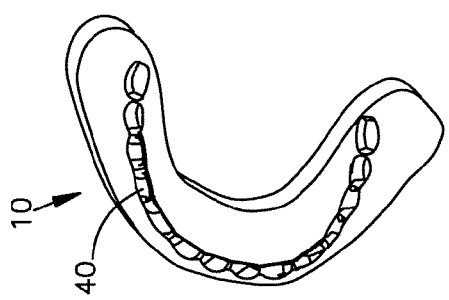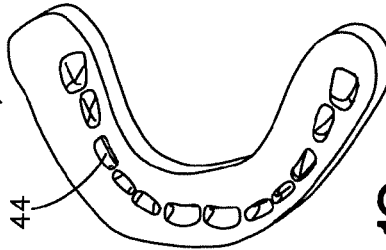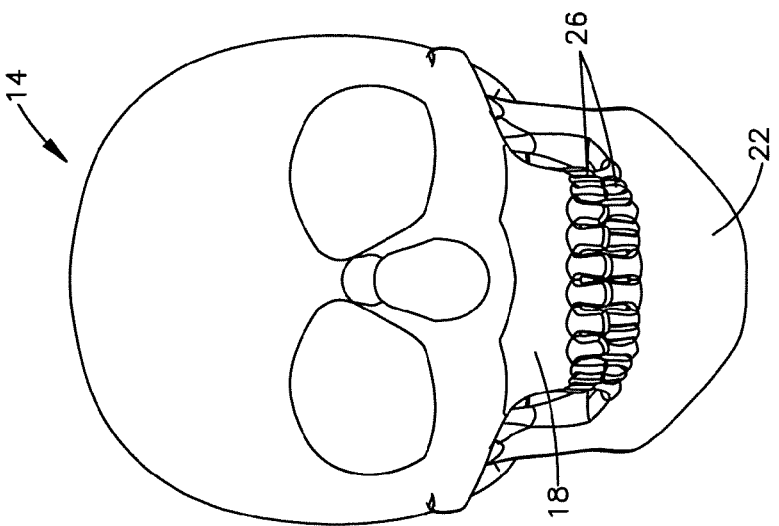

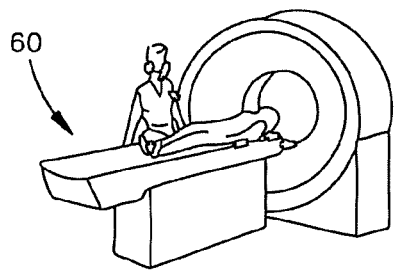
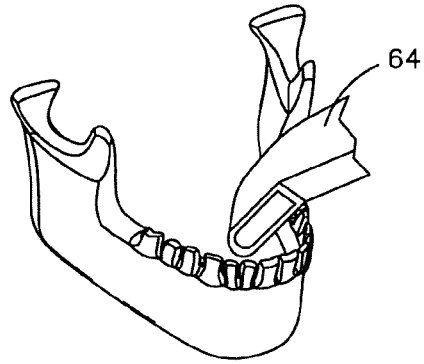
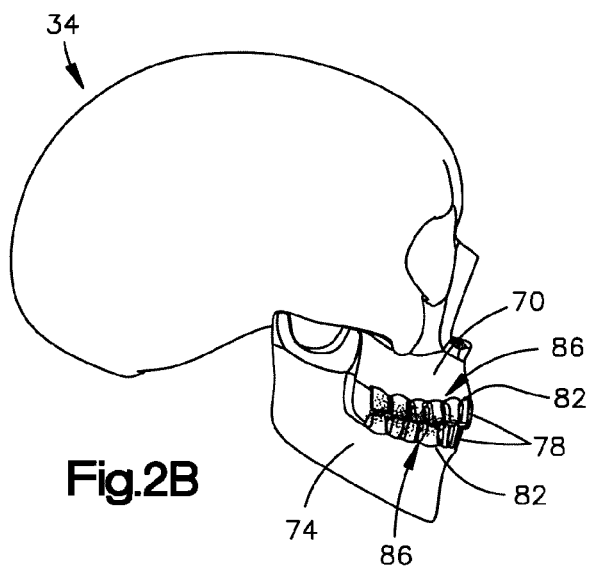
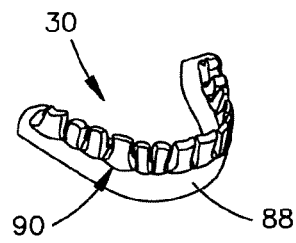
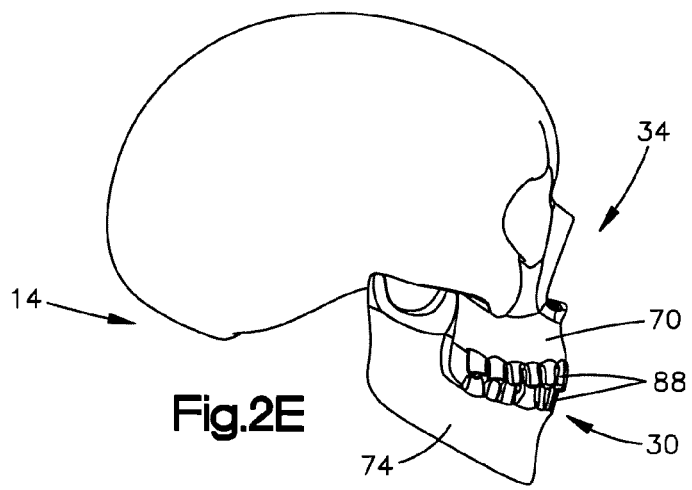

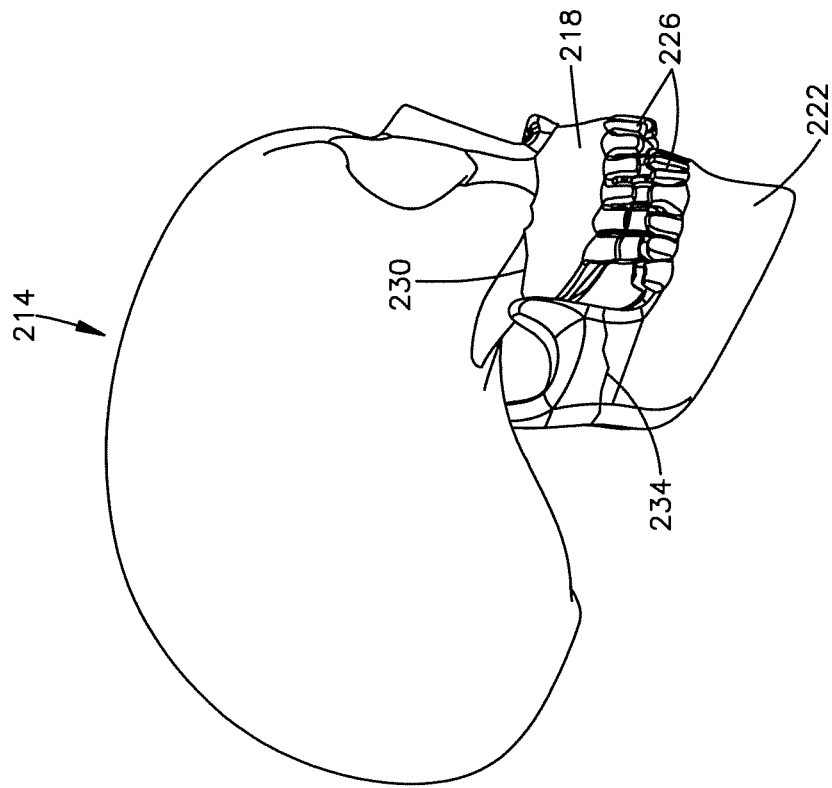
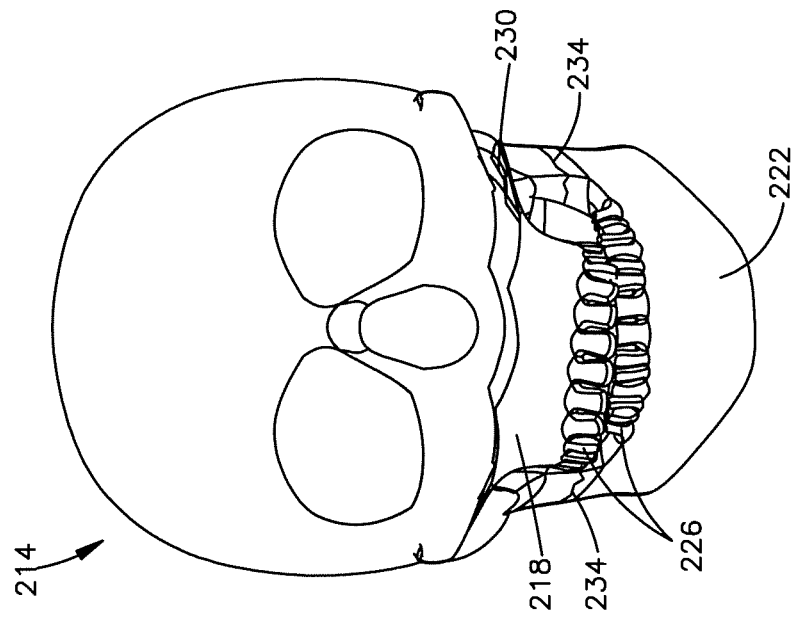

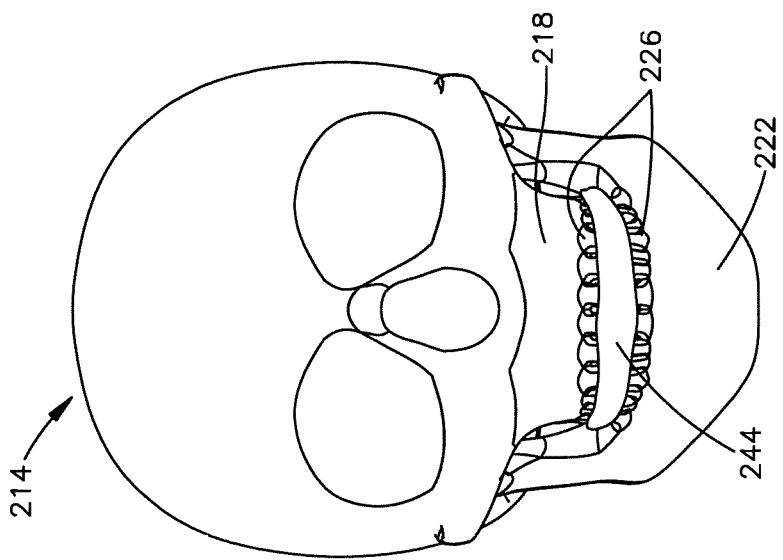
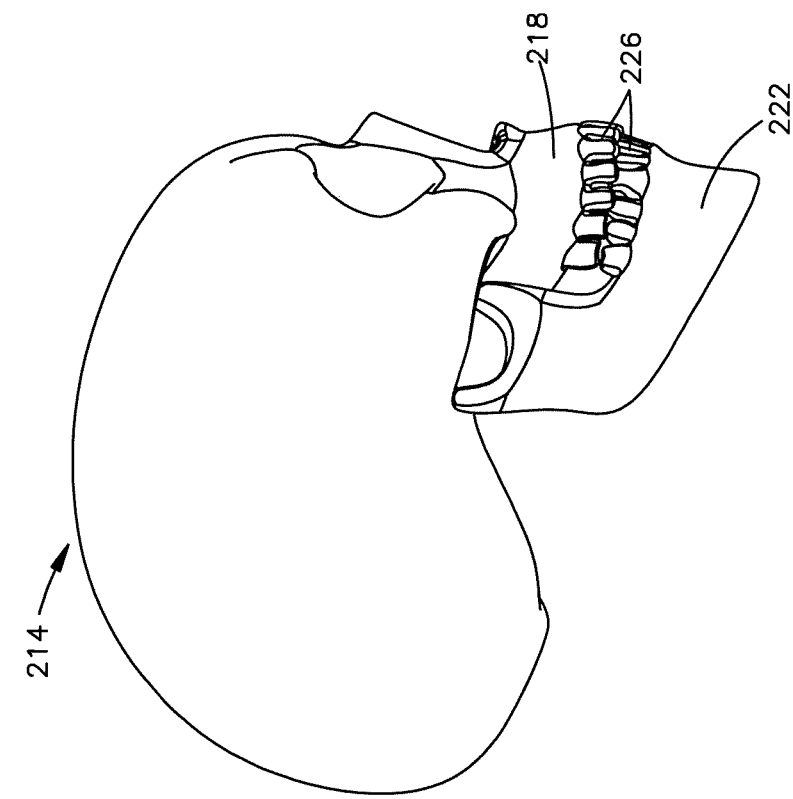

METHOD OF SURGICAL PLANNING

CROSS REFERENCE TO RELATED APPLICATIONS

This application claims the benefit of U.S. Provisional Application No. 61/648,226 filed May 17, 2012 the contents of which are hereby incorporated by reference in their entirety herein.

BACKGROUND

Surgical planning for orthognathic surgery traditionally combines various diagnostic methods to create a surgical plan and/or to construct a surgical splint that can transfer the surgical plan to the patient in the operating room. According to more recent methods, a 3-D computed tomography (CT) model of the patient's skull including the patient's mandible, maxilla, and dentition is obtained using a CT scanner. While the CT scanner provides a good representation of the patient's bone structure, it is not capable at times of accurately representing the patient's dentition (i.e. teeth). For example, the dentition represented in the CT model may be obscured or otherwise include "artifacts" due to orthodontic metal brackets, dental fillings, or prosthesis on or near the patient's dentition.

To create a 3-D computer model having a good representation of both the patient's bone structure and the patient's dentition, a dental computer model of the patient's dentition is typically obtained by scanning a negative of an impression (i.e. a plaster cast) of the patient's dentition with a laser scanner or a CT scanner. Because a plaster cast of the dentition, and not the dentition themselves is scanned, the virtual dental model is not obscured or otherwise "scattered" due to the metal brackets, fillings, or prosthesis. The virtual dental model is then combined with the CT model of the patient's skull to thereby form a composite computer model that has virtual dentition void of any artifacts. The composite computer model is used to create the surgical plan and/or surgical splint.

To align the dental computer model with the dentition of the CT model, metal fiduciary markers are currently used during both the CT scan of the patient's skull and the scan of the plaster cast. The fiduciary markers of the dental computer model are then aligned with the fiduciary markers of the CT model to form the composite computer model. While the current method is capable of forming a composite computer model that is used to create an orthognathic surgical plan and/or surgical splint, the method is time consuming. Moreover, there remains a desire for more accurate surgical plans and/or surgical splints than those currently provided.

SUMMARY

A method of pre-operatively forming a surgical splint configured to receive a patient's dentition can include combining a 3-D facial computer model and a 3-D dental computer model. The method includes the step of obtaining a 3-D facial computer model of at least the patient's maxilla, mandible, and dentition. The 3-D facial computer model includes first virtual dentition, wherein at least a portion of the first virtual dentition of the 3-D facial computer model has a first virtual surface geometry that defines at least one first fiduciary marker. The method further includes the step of obtaining a 3-D oral scan of a surface geometry of the patient's dentition so as to produce second virtual dentition. At least a portion of the second virtual dentition has a second surface geometry that defines at least one second fiduciary marker that corresponds to the at least one first fiduciary marker of the 3-D facial computer model. The second fiduciary marker can be aligned with the first fiduciary marker. After the alignment step, the first virtual dentition of the 3-D facial computer model can be replaced with the second virtual dentition to form a composite 3-D virtual model. The composite 3-D virtual model can have third virtual dentition in a planned post-operative configuration. A surgical splint can be custom constructed to match the planned post-operative shape. The surgical splint can have a negative impression of at least a portion of the third virtual dentition.

BRIEF DESCRIPTION OF THE DRAWINGS

The foregoing summary, as well as the following detailed description of example embodiments, are better understood when read in conjunction with the appended drawings. For the purpose of illustrating the invention, the drawings show embodiments that are presently preferred. The invention is not limited, however, to the specific instrumentalities disclosed in the drawings.

FIG. 1A is a perspective view of a composite 3-D virtual model of a patient's skull including a 3-D virtual representation of the patient's maxilla, mandible and dentition, the maxilla and mandible being positioned into a desired post-operative shape;

FIG. 1B is a top perspective view of a final surgical splint that is configured to align the patient's maxilla and mandible in the desired post-operative shape, the final surgical splint is custom constructed pre-operatively using the composite computer model of FIG. 1A;

FIG. 1C is a bottom perspective view of the final surgical splint shown in FIG. 1B;

FIG. 1D is a bottom perspective view of an intermediate surgical splint that is configured to align the patient's maxilla in its desired post-operative shape prior to the mandible being aligned in its desired post-operative shape, the intermediate surgical splint is constructed pre-operatively using the composite computer model of FIG. 1A;

FIG. 1E is a bottom perspective view of the intermediate surgical splint shown in FIG. 1D;

FIGS. 2A-2E illustrate steps of a method of creating the composite 3-D virtual model shown in FIG. 1A in accordance with an embodiment;

FIG. 4A is a front elevation view of a composite 3-D virtual model in a pre-operative shape, the composite 3-D virtual model having a virtual maxilla, a virtual mandible, and virtual dentition;

FIG. 4B is a side elevation view of the composite 3-D virtual model shown in FIG. 4A;

FIG. 4G is a side elevation view of the composite 3-D virtual model shown in FIG. 4F;

FIG. 4H is a front elevation view of the composite 3-D virtual model shown in FIG. 4F including a virtual final splint that receives the virtual dentition when both the virtual maxilla and the virtual mandible are in their post-operative shape;

DETAILED DESCRIPTION

Figure 3A:
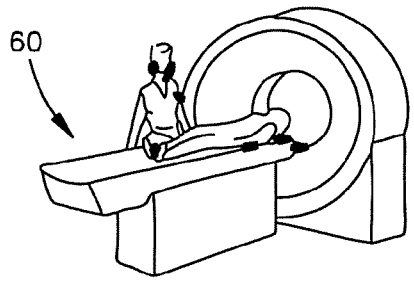
FIGS. 3A-3E illustrate steps of a method of creating the composite 3-D virtual model shown in FIG. 1A in accordance with another embodiment.
Figure 3C:
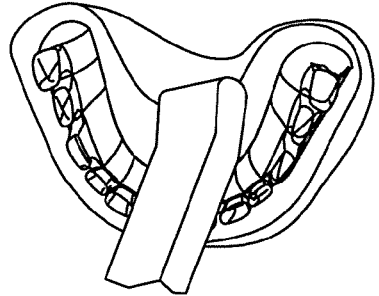
Figure 3B:
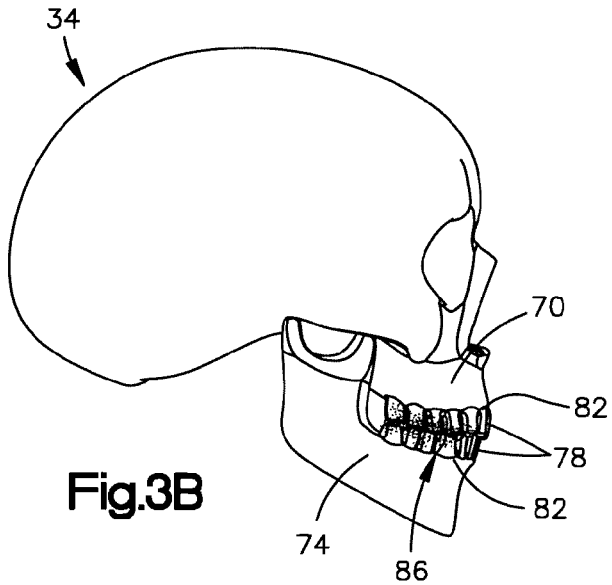
Figure 3D:
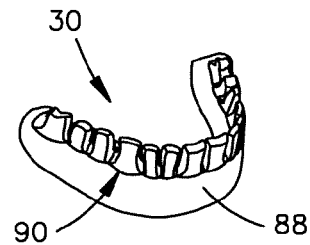
Figure 3E:
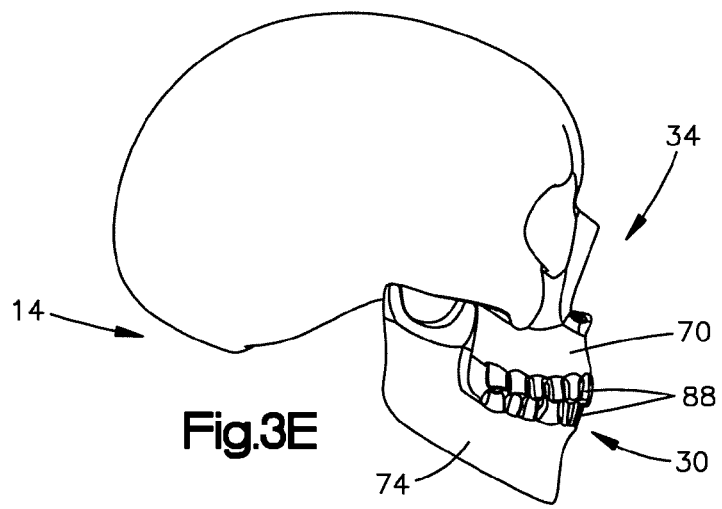

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases designate preferred positions and orientations in the human body to which reference is made and are not meant to be limiting. The terminology includes the above-listed words, derivatives thereof and words of similar import.

Referring to FIGS. 1A-1C, a first orthognathic surgical splint 10 can be custom constructed for an individual patient by creating a composite 3-D virtual model 14 of the patient's skull including at least a virtual representation of the patient's maxilla, mandible, and dentition. Therefore, the composite 3-D virtual model 14 can include a virtual maxilla 18, a virtual mandible 22, and virtual dentition 26. Using the composite 3-D virtual model 14, the surgical splint 10 can be custom constructed prior to the surgical operation (i.e. pre-operatively) to match or otherwise conform to a desired and planned post-operative shape of the patient's skull.

As will be described in reference to FIGS. 2A-2E, the composite 3-D virtual model 14 combines a 3-D dental computer model 30 obtained in a computer from an optical scan of a surface geometry of the patient's dentition with a separate 3-D facial computer model 34 obtained in the computer from a scan of the patient's skull. The 3-D dental computer model 30 and the 3-D facial computer model 34 are combined to thereby form the composite 3-D virtual model 14 that includes detailed bone information from the 3-D facial computer model 34 and detailed dentition information from the 3-D dental computer model 30.

Once created, the composite 3-D virtual model 14 can be manipulated into a desired post-operative shape by for example, adjusting the virtual maxilla 18 and/or the virtual mandible 22 of the composite 3-D virtual model 14 relative to the other to correct craniofacial/maxillofacial deformities and/or a cosmetic defect. Using the composite 3-D virtual model 14 after it has been manipulated into the planned post-operative shape, the orthognathic surgical plan and/or the surgical splint 10 can then be custom constructed to match the planned post-operative shape. For example, a computer model or virtual splint can be created in conjunction with the composite 3-D virtual model 14 to match the planned post-operative shape of the patient's skull. That is, a computer model or virtual splint can be created so as to be configured to receive the virtual dentition 26 after the virtual maxilla 18 and/or the virtual mandible 22 have been repositioned. Information from the computer model or virtual splint can then be transferred to a rapid prototyping machine where the actual surgical splint is fabricated. It should be appreciated, that the planned post-operative shape of the patient's skull can be substantially similar to the pre-operative shape of the patient's skull and that the surgical plan and/or surgical splint 10 can be constructed to aid in the correction of a portion of the patient's skull other than the maxilla and mandible. For example, the surgical plan and/or surgical splint 10 can be constructed to aid in the replacement of a tooth.

As shown in FIGS. 1B and 1C, the surgical splint 10 can include an upper surface 40 and a lower surface 44. The upper surface 40 can be configured to receive the upper dentition of the patient such as at least a portion of the upper dentition, and the lower surface 44 can be configured to receive the lower dentition of the patient such as at least a portion of the lower dentition when the patient's mandible and maxilla are in their post-operative shape or positions so as to define the post-operative shape of the patient's skull. That is, the upper surface 40 of the surgical splint 10 defines a negative impression having contours that correspond to the contours of the upper dentition of the patient when the upper dentition are received by the negative impression, and the lower surface 44 defines a negative impression having contours that correspond to the contours of the lower dentition of the patient when the lower dentition are received by the negative impression, and when both the patient's maxilla and the patient's mandible are properly positioned. Therefore, the upper surface 40 will match the upper dentition of the patient, and the lower surface 44 will match the lower dentition of the patient when both the patient's maxilla and the patient's mandible have been moved into their desired post-operative shape or positions. In this way, the surgical splint 10 acts as a guide for the orthognathic surgical plan such that the maxilla and the mandible can more easily be aligned into their desired post-operative positions during the surgery.

In certain cases and in reference to FIGS. 1C and 1D, a second orthognathic surgical splint 50 may be desired. For example, in cases where both the maxilla and the mandible of the patient are to be repositioned into a post-operative position or shape, the maxilla can be repositioned and affixed in its post-operative position prior to the mandible being repositioned. The surgical splint 50 can be configured to ensure that the repositioned maxilla is properly aligned into its post-operative position or shape prior to being affixed into position with bone screws.

Therefore, the surgical splint 50 can include an upper surface 54 configured to receive the upper dentition of the patient such as at least a portion of the dentition, and a lower surface 58 configured to receive the lower dentition of the patient such as at least a portion of the dentition when the patient's maxilla is in its post-operative shape or position, and the patient's mandible is in its pre-operative shape or position. That is, the upper surface 54 defines a negative impression having contours that correspond to the contours of the upper dentition of the patient when the upper dentition are received by the negative impression, and the lower surface 58 defines a negative impression having contours that correspond to the contours of the lower dentition of the patient when the lower dentition are received by the negative impression, and when the patient's maxilla is properly repositioned and prior to the mandible being repositioned. Therefore, the upper surface 54 will match the upper dentition of the patient, and the lower surface 58 will match the lower dentition of the patient when the patient's maxilla has been moved into its desired post-operative shape or position. In this way, the surgical splint 50 also acts as a guide for the orthognathic surgical plan. Once the maxilla is affixed to the skull, the mandible can be repositioned using the surgical splint 10. In this way, the surgical splint 10 can be considered a final surgical splint and the surgical splint 50 can be considered an intermediate surgical splint. It should be appreciated, however, that the mandible can be repositioned prior to the repositioning of the maxilla. Therefore, in cases where both the mandible and the maxilla are to be repositioned, the mandible can be repositioned first using the intermediate surgical splint 50, and the maxilla can be repositioned second using the final surgical splint 10.

Both the surgical splint 10 and the surgical splint 50 can be manufactured out of a plastic, such as acrylic. The surgical splints 10 and 50 can be machined or otherwise fabricated using a rapid prototyping machine such as a stereolithographic apparatus (SLA machine). The SLA machine can fabricate the surgical splints 10 and 50 based on the computer models or virtual splints created using the composite 3-D virtual model 14. It should be appreciated, however, that the surgical splints 10 and 50 can be manufactured out of any material as desired, and that the surgical splints 10 and 50 can be manufactured using any manufacturing method as desired.

FIGS. 2A-2E illustrate a method of forming the composite 3-D virtual model 14 used to create the surgical splints (i.e. surgical splints 10 and 50). The method can include all or some of the steps schematically represented as steps 2A, 2B, 2C, 2D, and 2E. To form the composite 3-D virtual model 14 and in reference to steps 2A and 2C, the 3-D facial computer model 34 and the 3-D dental computer model 30 can be obtained in a computer using respective scanning devices.

In step 2A, the 3-D facial computer model 34 can be obtained by scanning the patient's skull using any suitable technology. For example, the 3-D facial computer model of the patient's skull can be obtained by scanning the patient's skull using any suitable scanner 60, such as a CT or coronal view cone beam CT scan (CBCT) scanner as illustrated. It should be appreciated, however, that the 3-D facial computer model 34 may be obtained using technology other than a CT scanner, such as a laser scanning machine, an optical scanning machine, or an MRI machine. In operation, scanner 60 can be used to scan the patient's skull. Scanned data obtained from the scanner 60 can then be downloaded or transferred to a computer. In the computer, the 3-D facial computer model 34 representing the patient's skull is created from the scanned data using any suitable software capable of processing and editing images.

As shown in FIG. 2B, the 3-D facial computer model 34 can include at least a virtual maxilla 70, a virtual mandible 74, and virtual dentition 78. The virtual maxilla 70, virtual mandible 74, and virtual dentition are virtual representations of the patient's actual maxilla, actual mandible, and actual dentition. The virtual dentition 78 of the 3-D facial computer model 34, however, can be obscured or otherwise "scattered" (i.e. include artifacts) due to orthodontic metal brackets, dental fillings, or prosthesis that are proximate to the patient's actual dentition during the scan by the scanner 60. While the virtual dentition 78 may not have the desired accuracy, at least a portion 82 of the virtual dentition 78 has a first virtual surface geometry that defines a first fiduciary marker 86 that is substantially unobscured by the artifacts. That is, the at least a portion 82 of the virtual dentition 78 can have the necessary accuracy to define a point of reference so as to create a fiduciary marker 86 that can be later used to align the 3-D dental computer model 30 with the 3-D facial computer model 34. It should be appreciated, that the at least a portion 82 can be any portion of the virtual dentition 78. It should be further appreciated, that the virtual dentition 78 can have a first virtual surface geometry that defines any number of first fiduciary markers 86. For example, the virtual dentition 78 can have a first virtual surface geometry that defines at least three first fiduciary markers 86.

In step 2C, the 3-D dental computer model 30 of the patient's dentition can be obtained from a 3-D optical intraoral scan or otherwise intraorally imaging the patient's actual dentition with an intraoral scanner 64 such as with an optical scanner as illustrated. The scanned data can then be downloaded or transferred to a computer such as the same computer as the 3-D facial computer model 34. In the computer, the 3-D dental computer model 30 representing the patient's dentition is created using any suitable software capable of processing and editing images.

As shown in FIG. 2D, the 3-D dental computer model 30 more accurately depicts the patient's actual dentition as compared to the virtual dentition 78 depicted in the 3-D facial computer model 34. That is, the 3-D dental computer model 30 is substantially free from the artifacts that are produced in the 3-D facial computer model 34 by the scanner 60. As shown in FIG. 2D, the 3-D dental computer model 30 includes second virtual dentition 88 that have a second virtual surface geometry that defines at least one second fiduciary marker 90 that corresponds to the at least one first fiduciary marker 86 of the virtual dentition 78 of the 3-D facial computer model 34. In particular, the second virtual surface geometry of the virtual dentition 88 of the 3-D dental computer model 30 can define a second fiduciary marker 90 that corresponds to each first fiduciary marker 86 of the virtual dentition 78 of the 3-D facial computer model 34.

Unlike the scanner 60, the scanner 64 is configured to obtain 3-D surface information of the patient's dentition at a very high degree of accuracy and substantially without any artifacts. The scanner 64 is able to generate the 3-D surface information by moving the scanner directly over the patient's actual dentition. The scanner 64 obtains coordinates of points or pixels on the surface of the dentition being scanned, which are processed in a computer to calculate the surface configuration of the dentition and subsequently form the 3-D dental computer model 30. The scanner 64 can include an oscillating microelectromechanical systems (MEMS) mirror and a light source that emits a laser beam toward the oscillating MEMS mirror. The oscillating MEMS mirror reflects the emitted laser beam toward the surface of the patient's dentition. The surface of the patient's dentition then reflects the emitted laser beam back to a receiver of the scanner 64. A processing unit of the scanner 64 records timing parameters of the emitted laser beam and reflected laser beam, and oscillation angles of the oscillating MEMS mirror. The processing unit then computes the 3-D surface configuration of the patient's dentition and subsequently forms the 3-D dental computer model 30. It should be appreciated, however, that the 3-D dental computer model 30 can be obtained using any scanner capable of accurately creating an image of the patient's dentition that is substantially free from artifacts.

In step 2E, the 3-D dental computer model 30 and the 3-D facial computer model 34 can be combined to form the composite 3-D virtual model 14. The models 30 and 34 can be combined by aligning the at least one second fiduciary marker 90 of the virtual dentition 88 of the 3-D dental computer model 30 with the at least one first fiduciary marker 86 of the virtual dentition 78 of the 3-D facial computer model 34. The virtual dentition 78 of the 3-D facial computer model 34 are thus replaced with the more accurate virtual dentition 88 of the 3-D dental computer model 30 thereby creating a computer model that more accurately represents both the bony structure and the dentition of the patient. Therefore, the virtual maxilla 18, the virtual mandible 22, of the composite 3-D virtual model 14 are the same as the virtual maxilla 70, and the virtual mandible 74 of the 3-D facial computer model 34, and the virtual dentition 26 of the composite 3-D virtual model 14 are the same as the virtual dentition 88 of the 3-D dental computer model 30. It can also be said, however, that the virtual dentition 26 of the composite 3-D virtual model are third virtual dentition 26. Because the 3-D dental and facial computer models 30 and 34 are aligned using first and second fiduciary markers 86 and 90 that are defined by the virtual surface geometries of the virtual dentition of the 3-D dental and facial computer models 30 and 34, the models 30 and 34 are capable of being aligned without using metal fiduciary markers.

The combining step shown in FIG. 2E can be performed by a computer program having an algorithm that is capable of matching the fiduciary markers 86 and 90. While the computer program may be able to substantially align the fiduciary markers 86 and 90, some manual alignment may be required by the user by moving the virtual dentition 88 of the 3-D dental computer model 30 relative to the virtual dentition 78 of the 3-D facial computer model 34 with for example a computer mouse. It should be appreciated, however, that the fiduciary markers 86 and 90 can be aligned using any method as desired. For example, the user may completely align the fiduciary markers 86 and 90 without the use of a computer program as desired.

Once the composite 3-D virtual model 14 is created, the composite 3-D virtual model 14 can then be manipulated into a planned post-operative shape as desired. For example, at least one of the virtual maxilla 18 and the virtual mandible 22 can be repositioned relative to each other or the remainder of the virtual skull into a desired shape or position so as to properly align the third virtual dentition 26 of the composite 3-D virtual model 14 into the desired post-operative configuration. It can also be said, that the third virtual dentition can be displaced into the desired and planned post-operative configuration. Using the planned post-operative configuration of the virtual dentition 26 of the composite 3-D virtual model 14, the surgical splint(s) can be formed or otherwise fabricated pre-operatively so as to be able to receive the patient's actual dentition after the patient's actual maxilla and/or actual mandible have been repositioned into the planned-post operative shape. That is, the surgical splint(s) can be constructed to have a negative impression of a least a portion of the third virtual dentition 26. In this way, the surgical splint(s) can be custom constructed to match the planned post-operative shape prior to the surgery and act as a guide during the surgical procedure.

FIGS. 3A-3E illustrate a method of forming the composite 3-D virtual model 14 in accordance with another embodiment. The method illustrated in FIGS. 3A-3E can include all or some of the steps of the method illustrated in FIGS. 2A-2E and are schematically represented as steps 3A, 3B, 3C, 3D, and 3E. As shown in FIGS. 3A-3E, to form the composite 3-D virtual model 14 and in reference to steps 3A and 3C, the 3-D facial computer model 34 and the 3-D dental computer model 30 are obtained using respective scanning devices.

In step 3A, the 3-D facial computer model 34 is obtained in a similar manner as described in step 2A of the method illustrated in FIGS. 2A-2E. Therefore as in Step 2A, the 3-D facial computer model 34 of the patient's skull can be obtained in a computer by scanning the patient's skull using any suitable scanner 60, such as a CT or CBCT scanner as illustrated. Also as in Step 2A, the 3-D facial computer model 34 obtained by the scan includes at least the virtual maxilla 70, the virtual mandible 74, and first virtual dentition 78. As previously described, the first virtual dentition 78 of the 3-D facial computer model 34 can be obscured or otherwise "scattered" (i.e. include artifacts), however, at least a portion 82 of the first virtual dentition 78 can include a first virtual surface geometry that has the necessary accuracy to define a first fiduciary marker 86.

In step 3C, the 3-D dental computer model 30 of the patient's dentition can be obtained in the computer by scanning or otherwise imaging a negative impression 160 of the patient's actual dentition with the optical scanner 64 rather than directly scanning the patient's actual dentition as performed in step 2B of the method illustrated in FIGS. 2A-2E.

In step 3C, the negative impression 160 of the patient's actual dentition can be formed using any conventional method. For example, the negative impression 160 can be formed using plaster. It should be appreciated, however, that the impression 160 can be formed using any method as desired.

Once the negative impression 160 is formed, the optical scanner 64 can scan the impression 160 to thereby create the 3-D dental computer model 30. As with the model created in step 2B, the 3-D dental computer model 30 more accurately depicts the patient's actual dentition as compared to the virtual dentition 78 depicted in the 3-D facial computer model 34. That is, the 3-D dental computer model 30 is substantially free from the artifacts that are produced in the 3-D facial computer model 34 by the scanner 60. The 3-D dental computer model 30 obtained in step B2 also includes second virtual dentition 88 that have a second virtual surface geometry that defines at least one second fiduciary marker 90 that corresponds to the at least one first fiduciary marker 86 of the first virtual dentition 78 of the 3-D facial computer model 34.

In step 3E, the 3-D dental computer model 30 and the 3-D facial computer model 34 can be combined to form the composite 3-D virtual model 14 in the same manner described in relation to step 2E. That is, the models 30 and 34 can be combined by aligning the at least one second fiduciary marker 90 of the second virtual dentition 88 of the 3-D dental computer model 30 with the at least one first fiduciary marker 86 of the first virtual dentition 78 of the 3-D facial computer model 34.

Figure 4D:
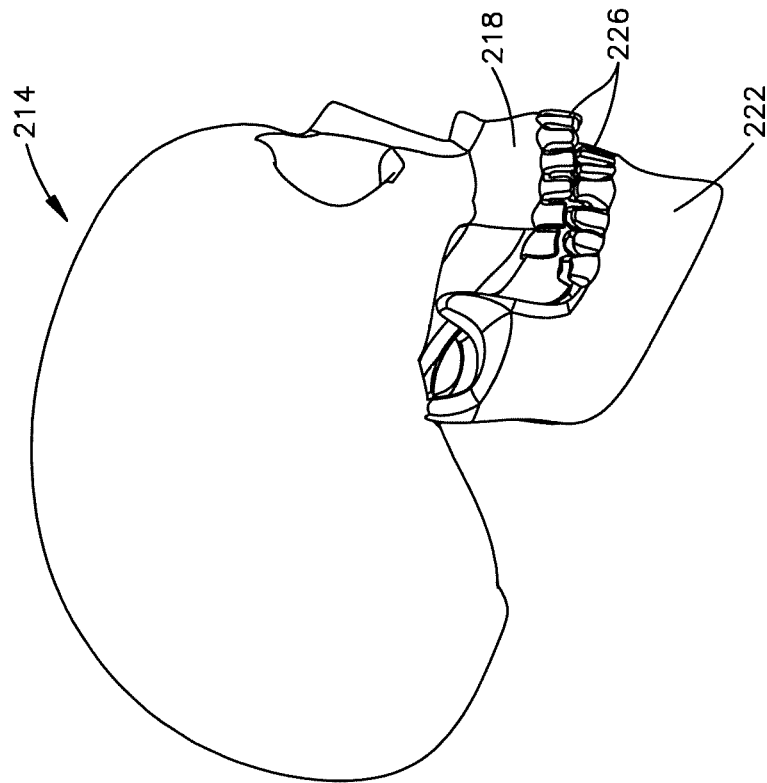
FIG. 4D is a side elevation view of the 3-D composite computer shown in FIG. 4C.

Now in reference to FIGS. 4A-4H, a method of custom constructing surgical splints, such as surgical splints 10 and 50 using a composite computer model created using one of the methods described in FIGS. 2 and 3 is illustrated. The method can be used to make both the intermediate surgical splint 50 and the final surgical splint 10 or can be used to make only one of the surgical splints 10 and 50 as desired. Therefore, the method can include all or some of the steps schematically represented in FIGS. 4A-4H, As shown in FIGS. 4A and 4B, a composite 3-D virtual model 214 can include a virtual maxilla 218, a virtual mandible 222, and third virtual dentition 226. The composite 3-D virtual model 214 can be obtained using any of the methods described in FIGS. 2A-2E and 3A-3E. As shown, the composite 3-D virtual model 214 originally represents the pre-operative shape of the patient's skull. In the illustrated example, the composite 3-D virtual model 214 indicates that the patient's dentition is not aligned and that as a result, the patient's maxilla and mandible need to be translated and rotated. Though it should be appreciated, that the patient's maxilla and/or mandible can be manipulated in any manner desired.

Figure 4C:
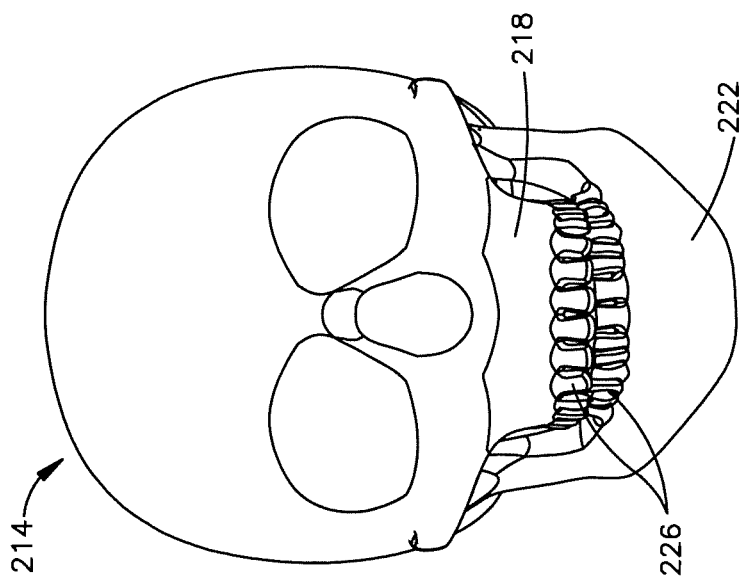
FIG. 4C is a front elevation view of the composite 3-D virtual model shown in FIG. 4A in an intermediate shape, the virtual maxilla being repositioned into its post-operative shape while the virtual mandible remains in its pre-operative shape.

With continued reference to FIGS. 4A and 4B, first and second virtual osteotomies 230 and 234 can be performed on the virtual maxilla 218 and virtual mandible 222 of the composite 3-D virtual model 214. As shown in FIGS. 4C and 4D the composite 3-D virtual model 214 can be manipulated into a desired intermediate shape. For example, the virtual maxilla 218 can be repositioned into its desired post-operative shape or position while the virtual mandible 222 remains in its pre-operative shape or position to thereby define an intermediate shape of the skull. As shown, the virtual maxilla 218 can be rotated and advanced forward a desired amount as illustrated to thereby reposition the virtual maxilla 218 into the desired post-operative shape or position. It should be appreciated, however, that the virtual maxilla 218 can be repositioned in any manner necessary to place the virtual maxilla 218 into its desired post-operative shape or position or configuration.

Figure 4F:
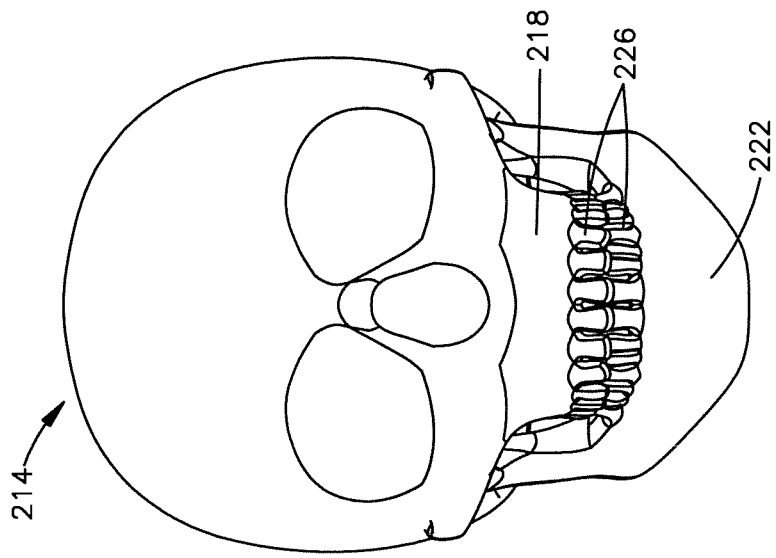
FIG. 4F is a front elevation view of the composite 3-D virtual model shown in FIG. 4C in a final post-operative shape, the virtual mandible being repositioned into its post-operative shape along with the virtual maxilla.
Figure 4E:
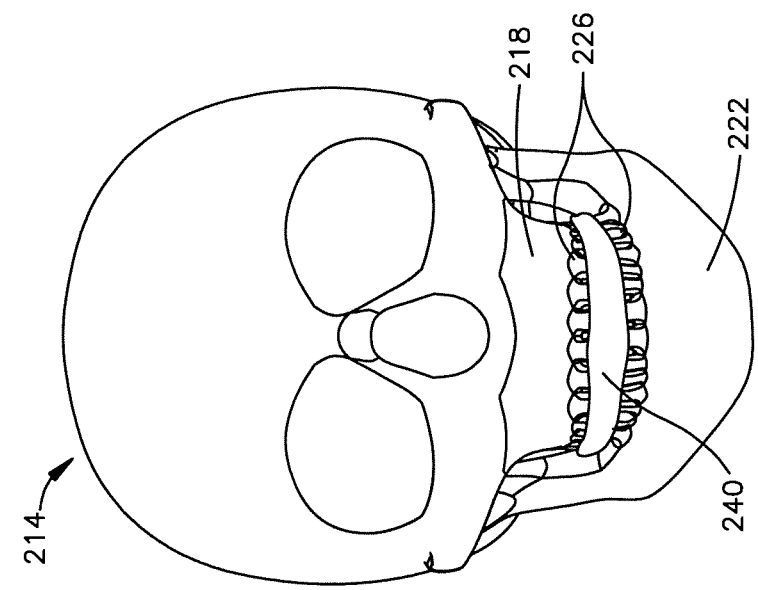
FIG. 4E is a front elevation view of the composite 3-D virtual model shown in FIG. 4C including a virtual intermediate splint that receives the virtual dentition when the virtual maxilla is in its post-operative shape and the virtual mandible is in its pre-operative shape.

While the composite 3-D virtual model 214 is in its intermediate shape, and thus prior to repositioning the virtual mandible 222, a virtual intermediate surgical splint 240 can be created to match the intermediate shape of the composite 3-D virtual model 214, for example as shown in FIG. 4E. That is, the virtual intermediate surgical splint 240 can be created such that the virtual intermediate surgical splint 240 receives the third virtual dentition 226 when the virtual maxilla 216 is in its post-operative shape or position and the virtual mandible 222 is in its pre-operative shape or position. Using the data from the virtual intermediate surgical splint 240 the physical or actual intermediate splint (i.e. surgical splint 50 shown in FIGS. 1C and 1D) can be fabricated on a rapid prototyping machine. In this way, the actual intermediate splint is fabricated to match the virtual intermediate splint. It can also be said, that the actual intermediate splint is constructed to have a negative impression of at least a portion of the third virtual dentition 226 when the third virtual dentition are in an intermediate configuration. Therefore, the actual intermediate splint can be used during the surgery to reposition the patient's actual maxilla into the desired post-operative shape or position as planned on the composite 3-D virtual model 214.

As shown in FIGS. 4F and 4G the composite 3-D virtual model 214 can be manipulated into a desired final or post-operative shape. For example, with the virtual maxilla 218 already repositioned into its desired post-operative shape or position or configuration, the virtual mandible 222 can now be repositioned into its desired post-operative shape or position or configuration to thereby define the final post-operative shape of the skull. As shown, the virtual mandible 222 can be rotated and advanced forward a desired amount as illustrated to thereby reposition the virtual mandible 222 into the desired post-operative shape or position. It should be appreciated, however, that the virtual mandible 222 can be repositioned in any manner necessary to place the virtual mandible 222 into its desired post-operative shape or position.

While the composite 3-D virtual model 214 is in its final or post-operative shape, a virtual final surgical splint 244 can be created to match the desired post-operative shape of the composite 3-D virtual model 214. That is, the virtual final surgical splint 244 can be created such that the virtual final surgical splint 244 receives the third virtual dentition 226 when both the virtual maxilla 216 and the virtual mandible 222 are in their post-operative shapes or positions or configurations. Using the data from the virtual final surgical splint 244 the physical or actual final splint (i.e. surgical splint 10 shown in FIGS. 1B and 1C) can be fabricated on a rapid prototyping machine. In this way, the actual final surgical splint is fabricated to match the virtual final surgical splint. It can also be said, that the actual final splint is constructed to have a negative impression of at least a portion of the third virtual dentition 226 when the third virtual dentition are in a final post-operative configuration. Therefore, the actual final surgical splint can be used during the surgery as a guide to reposition the patient's actual mandible into the desired post-operative shape or position as planned on the composite 3-D virtual model 214. It should be appreciated, however, that in some cases only a single surgical splint may be desired to reposition the patient's mandible and/or the patient's maxilla. Moreover, it should be appreciated that a surgical splint may be custom constructed to be a guide for a surgical procedure that does not involve repositioning the patient's maxilla and/or the patient's mandible. For example, a surgical splint may be custom constructed to be a guide for a surgical procedure that requires the placement of a tooth implant.

Figure 5:
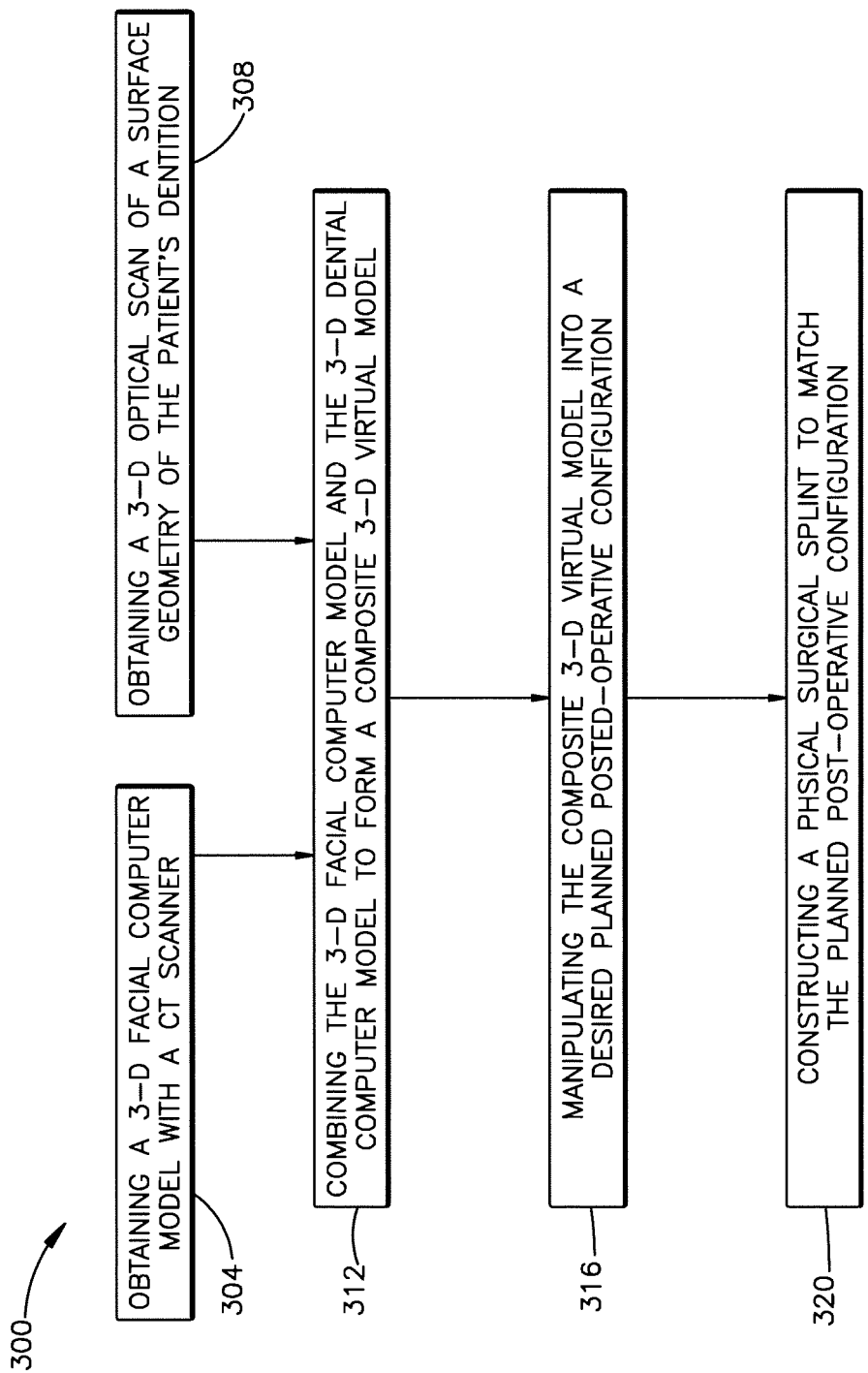
FIG. 5 is a flow chart that describes a method of custom constructing a surgical splint in accordance with an embodiment.

With reference to FIG. 5, a method 300 of pre-operatively forming a surgical splint configured to receive a patient's dentition when the patient's skull is in a desired post-operative shape can include steps 304, 308, 312, 316, and 320. In step 304 a 3-D facial computer model of at least the patient's maxilla, mandible, and dentition can be obtained in a computer. The 3-D facial computer model can include first virtual dentition, and at least a portion of the first virtual dentition of the 3-D facial computer model can have a first virtual surface geometry that defines at least one first fiduciary marker. In step 308, a 3-D dental computer model of the patient's dentition that more accurately depicts the patient's dentition as compared to the dentition depicted in the 3-D facial computer model is produced by obtaining a 3-D optical scan of a surface geometry of the patient's dentition. The 3-D dental computer model can include second virtual dentition that can have a second surface geometry that defines at least one second fiduciary marker that corresponds to the at least one first fiduciary marker of the 3-D facial computer model. In step 312, the 3-D dental computer model and the 3-D facial computer model can be combined to form a composite 3-D virtual model by aligning the at least one second fiduciary marker of the 3-D dental computer model with the corresponding at least one first fiduciary marker of the 3-D facial computer model. In step 316, the composite computer model can be manipulated into a planned post-operative shape. In step 320 a physical surgical splint can be pre-operatively custom constructed to match the planned post-operative shape, and the physical surgical splint can be configured to receive the patient's dentition when the patient's skull is in the desired post-operative shape.

In step 304, the 3-D facial computer model can be obtained in a computer by scanning the patient's skull with a CT scanner. In step 308, the 3-D dental computer model can be obtained in the computer by intraorally imaging the patient's dentition. For example, the 3-D dental computer model can be obtained by directly scanning the patient's dentition with an intraoral scanner, such as an optical scanner. In step 312, the 3-D dental computer model and the 3-D facial computer model can be combined without the use of metal fiduciary markers. In step 316 the composite computer model can be manipulated by repositioning at least one of the virtual maxilla and the virtual mandible. The method of FIG. 5 can further include the step of creating a virtual surgical splint model to match the planned post-operative shape, and the step of custom constructing the surgical splint comprises fabricating the surgical splint to match the virtual surgical splint model.

Figure 6:
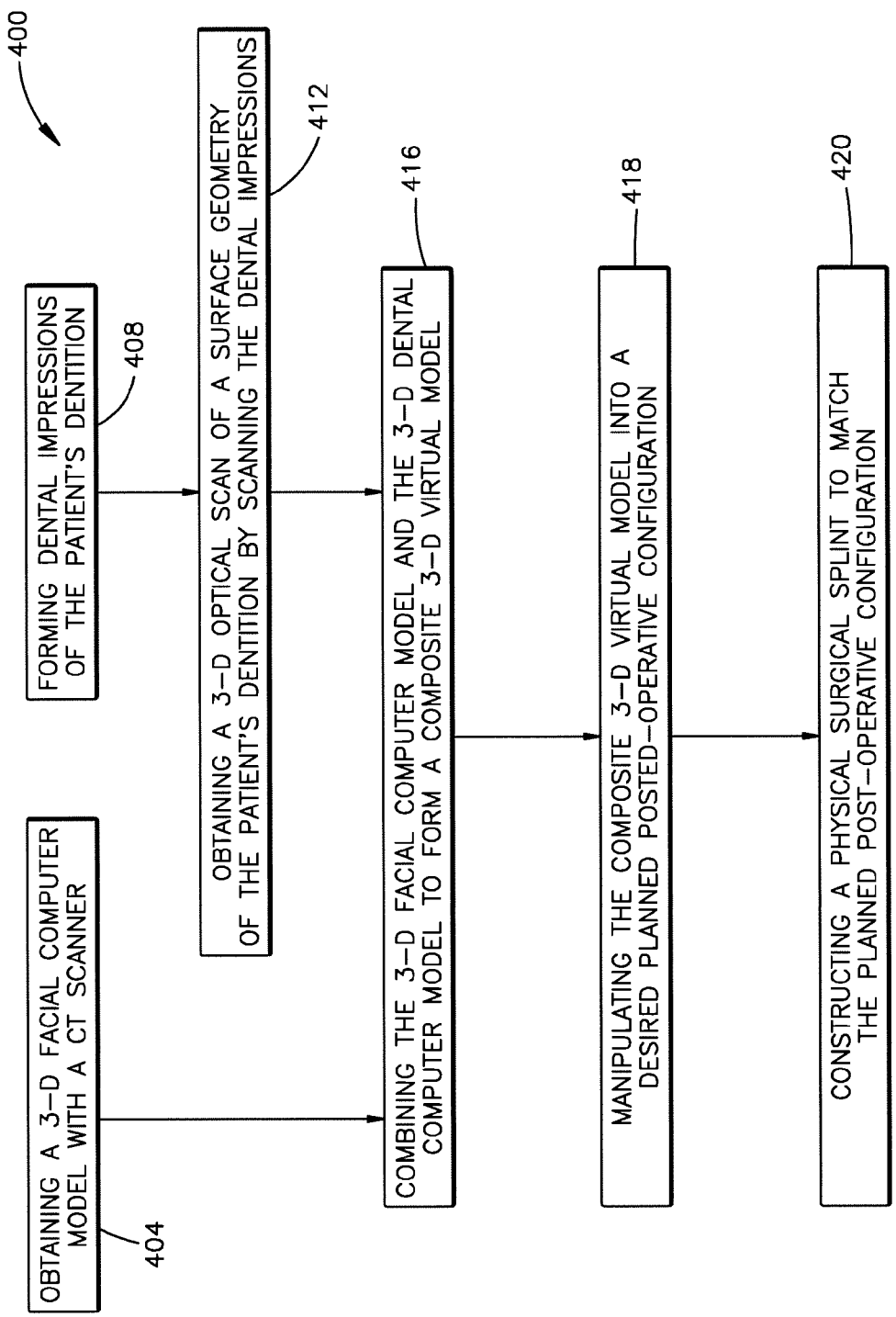
FIG. 6 is a flow chart that describes a method of custom constructing a surgical splint in accordance with another embodiment.

With reference to FIG. 6, a method 400 of pre-operatively forming a surgical splint configured to receive a patient's dentition when the patient's skull is in a desired post-operative shape can include steps 404, 408, 412, 416, 418 and 420. In step 404 a 3-D facial computer model of at least the patient's maxilla, mandible, and dentition can be obtained in a computer. The 3-D facial computer model can include virtual dentition, wherein at least a portion of the virtual dentition of the 3-D facial computer model has a first virtual surface geometry that defines at least one first fiduciary marker. In step 408, a dental impression of the patient's dentition can be formed. In step 412, a 3-D dental computer model of the patient's dentition can be obtained in a computer by scanning the dental impression with an optical scanner. The 3-D dental computer model can include second virtual dentition, wherein the second virtual dentition of the 3-D dental computer model have a second virtual surface geometry that defines at least one second fiduciary marker that corresponds to the at least one first fiduciary marker of the 3-D facial computer model. In step 416, the 3-D dental computer model and the 3-D facial computer model can be combined to form a composite 3-D virtual model by aligning the at least one second fiduciary marker of the 3-D dental computer model with the corresponding at least one first fiduciary marker of the 3-D facial computer model. In step 418, the composite computer model can be manipulated into a planned post-operative shape. In step 420 a surgical splint can be custom constructed to match the planned post-operative shape. The surgical splint can be configured to receive the patient's dentition. In step 416, the first virtual dentition of the 3-D facial computer model can be combined with the second virtual dentition of the 3-D dental computer model without the use of metal fiduciary markers.

It should be noted that the illustrations and discussions of the embodiments shown in the figures are for exemplary purposes only, and should not be construed limiting the disclosure. One skilled in the art will appreciate that the present disclosure contemplates various embodiments. For example, although the present disclosure refers to three-dimensional computer models, it is envisioned that any of the computer models described in the present disclosure can be two-dimensional. It should be further appreciated that the features and structures described and illustrated in accordance with one embodiment can apply to all embodiments as described herein, unless otherwise indicated. Additionally, it should be understood that the concepts described above with the above-described embodiments may be employed alone or in combination with any of the other embodiments described above.

What is claimed:

1. A method of pre-operatively forming a surgical splint configured to receive a patient's dentition when the patient's skull is in a post-operative shape, the method comprising:
    obtaining a 3-D facial computer model in a computer of at least the patient's maxilla, mandible, and dentition, the 3-D facial computer model including first virtual dentition, wherein at least a portion of the first virtual dentition has a first virtual surface geometry that defines at least one first fiduciary marker, the at least one first fiduciary marker defining a first location that identifies a first anatomical feature of the first virtual dentition;
    obtaining a 3-D optical intra-oral scan of the patient's dentition in the computer so as to produce second virtual dentition, wherein at least a portion of the second virtual dentition has a second surface geometry that defines at least one second fiduciary marker, the at least one second fiduciary marker defining a second location that identifies a second anatomical feature of the second virtual dentition;
    aligning the first fiduciary marker with the second fiduciary marker;
    after the aligning step, replacing the first virtual dentition of the 3-D facial computer model with the second virtual dentition to form a composite 3-D virtual model, the composite 3-D virtual model having third virtual dentition in a planned post-operative configuration; and
    constructing a surgical splint having a negative impression of at least a portion of the third virtual dentition.

2. The method of claim 1, wherein the step of obtaining a 3-D optical intra-oral scan of the surface geometry of the patient's dentition comprises the step of intraorally imaging the patient's dentition.

3. The method of claim 1, wherein after the replacing step, displacing the third virtual dentition into the planned post-operative configuration.

4. The method of claim 3, wherein the third virtual dentition includes maxillary dentition and mandibular dentition, and the displacing step comprises displacing one of the maxillary dentition and the mandibular dentition without displacing the other of the maxillary dentition and the mandibular dentition.

5. The method of claim 1, wherein the constructing step further comprises forming a negative impression of at least a portion of both the maxillary dentition and at least a portion of the mandibular dentition in the surgical splint.

6. The method of claim 1, wherein the first virtual surface geometry defines at least three first fiduciary markers, and the second virtual dentition has a second surface geometry that defines at least three second fiduciary markers.

7. The method of claim 1, wherein the step of obtaining a 3-D facial computer model comprises scanning the patient's skull with a CT scanner.

8. The method of claim 1, wherein the composite 3-D virtual model includes a virtual maxilla and a virtual mandible, and further comprising the step of manipulating the composite 3-D virtual model into the post-operative configuration by repositioning at least one of the virtual maxilla and the virtual mandible.

9. The method of claim 1, further comprising the step of creating a virtual surgical splint model to match the third virtual dentition, wherein the step of constructing the surgical splint comprises fabricating the surgical splint to correspond to the virtual surgical splint model.

10. The method of claim 1, wherein the step of aligning the first fiduciary marker with the second fiduciary marker is accomplished without the use of metal fiduciary markers.

11. The method of claim 1, wherein the third virtual dentition is identical to the second virtual dentition.

12. The method of claim 1, wherein the second virtual dentition more accurately depicts the patient's actual dentition than the first virtual dentition.

13. A method of pre-operatively forming a surgical splint configured to receive a patient's dentition when the patient's skull is in a post-operative shape, the method comprising:
    obtaining a 3-D facial computer model in a computer of at least the patient's maxilla, mandible, and dentition, the 3-D facial computer model including first virtual dentition, wherein at least a portion of the first virtual dentition has an anatomical feature that defines at least one first fiduciary marker;
    obtaining a 3-D optical scan of the patient's dentition in the computer, wherein the 3-D optical intraoral scan includes second virtual dentition, wherein at least a portion of the second virtual dentition has a second anatomical feature that defines at least one second fiduciary marker that corresponds to the first anatomical feature;
    aligning the first fiduciary marker with the second fiduciary marker;
    after the aligning step, replacing the first virtual dentition of the 3-D facial computer model with the second virtual dentition to thereby form a composite 3-D virtual model having third virtual dentition;

manipulating the composite 3-D virtual model into a planned post-operative configuration; and custom constructing a surgical splint to having a negative impression of at least a portion of the third virtual dentition when in the planned post-operative configuration.

14. The method of claim 13, wherein the step of obtaining a 3-D facial computer model comprises scanning the patient's skull with a CT scanner.

15. The method of claim 13, wherein the composite 3-D virtual model includes a virtual mandible and a virtual maxilla, and the step of manipulating the composite 3-D virtual model comprises repositioning at least one of the virtual maxilla and the virtual mandible.

16. The method of claim 13, further comprising the step of creating a virtual surgical splint model to match the third virtual dentition, wherein the step of custom constructing the surgical splint comprises fabricating the surgical splint to correspond to the virtual surgical splint model.

17. The method of claim 13, wherein the step of aligning the first fiduciary marker with the second fiduciary marker is accomplished without the use of metal fiduciary markers.

18. The method of claim 13, wherein the third virtual dentition is identical to the second virtual dentition.

19. The method of claim 13, wherein the step of obtaining the 3-D optical scan of the patient's dentition in the computer comprises a step of imaging dental impressions of the patient's dentition.

20. The method of claim 13, wherein the step of obtaining the 3-D optical scan of the patient's dentition in the computer comprises obtaining a 3-D optical intraoral scan of the patient's dentition in the computer.

* * * * *